US011925318B2

United States Patent
Matsuda

(10) Patent No.: US 11,925,318 B2
(45) Date of Patent: Mar. 12, 2024

(54) ENDOSCOPE

(71) Applicants: Fujikura Ltd., Tokyo (JP); FiberTech Co., Ltd., Sakura (JP)

(72) Inventor: Yusuke Matsuda, Sakura (JP)

(73) Assignees: Fujikura Ltd., Tokyo (JP); FiberTech Co., Ltd., Chiba (JP)

( * ) Notice: Subject to any disclaimer, the term of this patent is extended or adjusted under 35 U.S.C. 154(b) by 0 days.

(21) Appl. No.: 17/211,137

(22) Filed: Mar. 24, 2021

(65) Prior Publication Data

US 2021/0298575 A1 Sep. 30, 2021

(30) Foreign Application Priority Data

Mar. 26, 2020 (JP) ................. 2020-056095

(51) Int. Cl.
*A61B 1/00* (2006.01)
*A61B 1/05* (2006.01)
*A61B 1/06* (2006.01)
*A61B 1/07* (2006.01)

(52) U.S. Cl.
CPC ...... *A61B 1/00128* (2013.01); *A61B 1/00009* (2013.01); *A61B 1/00066* (2013.01); *A61B 1/07* (2013.01); *A61B 1/051* (2013.01); *A61B 1/0684* (2013.01)

(58) Field of Classification Search
CPC ... A61B 1/00128; A61B 1/00066; A61B 1/07; A61B 1/00009; A61B 1/051; A61B 1/0684; A61B 1/00144; A61B 1/042; A61B 1/00142; A61B 1/00105
See application file for complete search history.

(56) References Cited

U.S. PATENT DOCUMENTS

| | | | |
|---|---|---|---|
| 4,534,339 A * | 8/1985 | Collins | A61B 1/00128 600/146 |
| 5,190,028 A * | 3/1993 | Lafferty | A61B 1/317 600/920 |
| 6,203,494 B1 | 3/2001 | Moriyama | |
| 2002/0010385 A1* | 1/2002 | Ishibiki | A61B 1/00105 600/130 |
| 2003/0004460 A1* | 1/2003 | Bedell | A61B 1/00105 604/95.04 |
| 2008/0118212 A1* | 5/2008 | Tanaka | A61B 1/0011 65/408 |
| 2011/0009694 A1* | 1/2011 | Schultz | A61B 1/317 600/109 |
| 2017/0135561 A1* | 5/2017 | Snoke | A61B 17/42 |
| 2019/0282071 A1* | 9/2019 | Ouyang | A61B 1/0684 |
| 2022/0192471 A1* | 6/2022 | Levy | A61B 1/0615 |

FOREIGN PATENT DOCUMENTS

| | | |
|---|---|---|
| JP | S57-190546 A | 11/1982 |
| JP | H06-030894 A | 2/1994 |
| JP | H07-023892 A | 1/1995 |
| JP | 2003-135368 A | 5/2003 |
| JP | 2013-220325 A | 10/2013 |
| JP | 2018-538069 A | 12/2018 |

* cited by examiner

*Primary Examiner* — Aaron B Fairchild
(74) *Attorney, Agent, or Firm* — Osha Bergman Watanabe & Burton LLP

(57) ABSTRACT

An endoscope includes an endoscope operation unit; an insertion observation unit extending forward from the endoscope operation unit in a longitudinal direction of the endoscope; a coupling portion between the endoscope operation unit and the insertion observation unit; and an elastic body that covers at least a coupling portion.

3 Claims, 6 Drawing Sheets

ENDOSCOPE

CROSS-REFERENCE TO RELATED APPLICATIONS

Priority is claimed from Japanese Patent Application No. 2020-056095, filed on Mar. 26, 2020, the content of which is incorporated herein by reference.

TECHNICAL FIELD

The present invention relates to an endoscope.

BACKGROUND

PCT International Application Publication No. 2018-538069 of the PCT International Publication for Patent Applications discloses an endoscope including a tip probe (insertion observation unit) having a laser guide, an illumination guide, and an image guide and allowing these guides to pass therethrough, and a handpiece (endoscope operation unit) that is an operation unit supporting the probe.

In such an endoscope, the tip of the insertion observation unit extending forward from the endoscope operation unit is inserted into the body. After the insertion of the insertion observation unit, the endoscope operation unit is held and the tip thereof is directed toward the observation unit to observe the inside of the body. However, in that case, when the endoscope operation unit is suddenly moved, or the insertion observation unit is moved and the insertion observation unit is brought into contact with part of the body, a sudden bending stress is added to the insertion observation unit. In a structure in which the insertion observation unit that is a rigid body and the endoscope operation unit that is a rigid body are coupled to each other at a base end of the insertion observation unit as in the above related art, stress is likely to be concentrated on a coupling portion that couples the insertion observation unit with the endoscope operation unit. Depending on the case, there is a concern that the insertion observation unit is damaged.

SUMMARY

One or more embodiments of the present invention suppress damage to an insertion observation unit due to the operation of an endoscope.

An endoscope according to one or more embodiments of the present invention includes an endoscope operation unit; an insertion observation unit that extends forward from the endoscope operation unit; and an elastic body that covers at least a coupling portion between the endoscope operation unit and the insertion observation unit.

According to this configuration, even in a structure in which the rigid insertion observation unit and the endoscope operation unit that is a rigid body are coupled to each other at the base end of the insertion observation unit, the elastic body is disposed so as to cover the coupling portion between the endoscope operation unit and the insertion observation unit. Therefore, when an external force is applied to the insertion observation unit, it is possible to suppress the concentration of stress on the base end of the insertion observation unit.

In the above endoscope, the elastic body may have a tapered portion that is tapered toward the front.

In the above endoscope, the endoscope operation unit may have a holding portion molded integrally with the elastic body.

In the above endoscope, the insertion observation unit may have an illumination fiber that emits illumination light forward from a tip, the endoscope operation unit may have a case in which a wiring groove of the illumination fiber is formed, and the elastic body may have a filling portion for filling the wiring groove in which the illumination fiber is wired.

According to one or more embodiments of the present invention, any damage to the insertion observation unit due to the operation of the endoscope can be suppressed.

DETAILED DESCRIPTION

Hereinafter, embodiments of the present invention will be described with reference to the drawings. In the following description, an ophthalmic electronic endoscope will be exemplified.

First, an overall outline of the endoscope 1 will be described.

Figure 1:
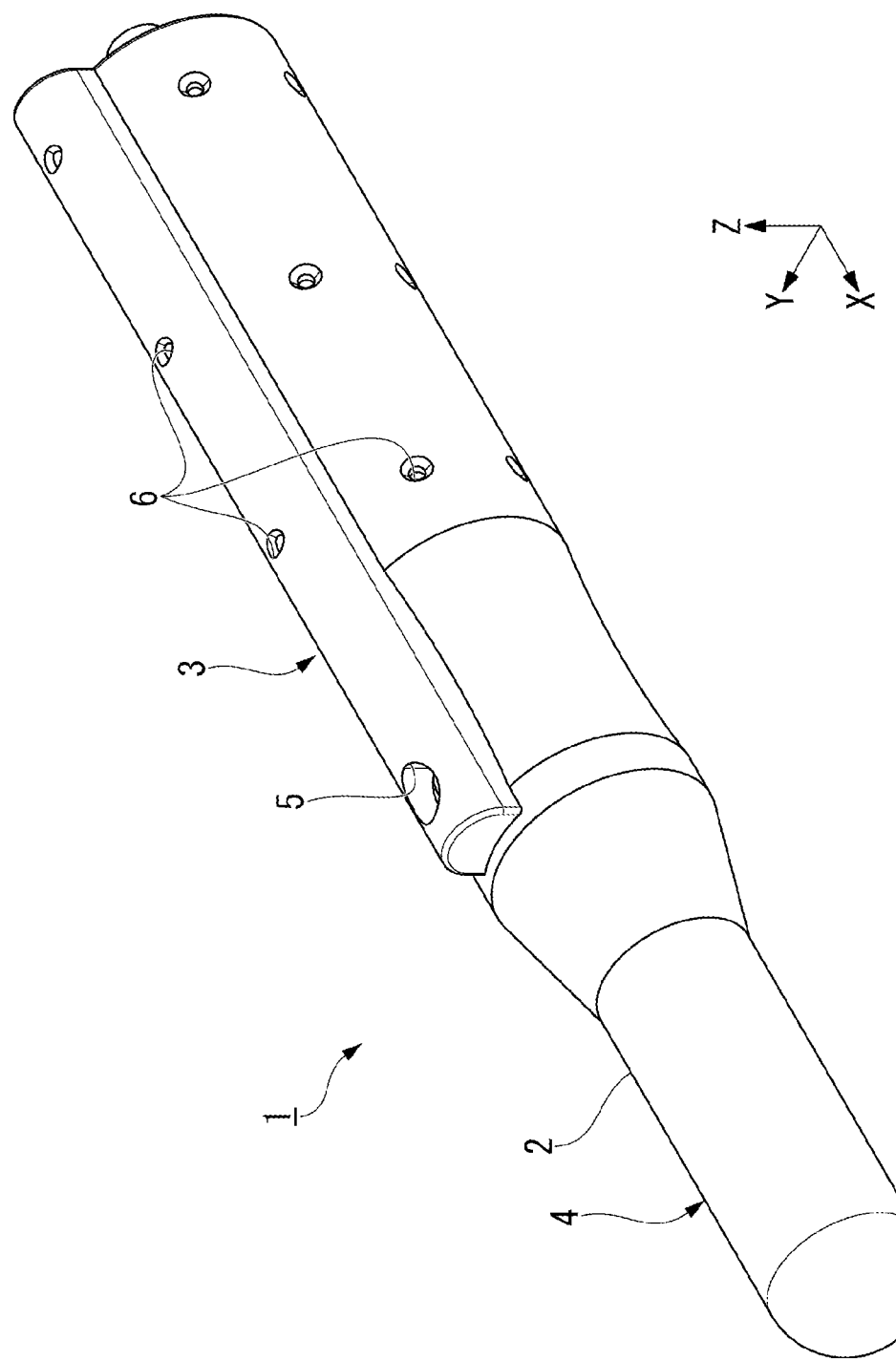
FIG. 1 is a perspective view of an endoscope mounted with a protective cap according to one or more embodiments of the present invention.
Figure 2:
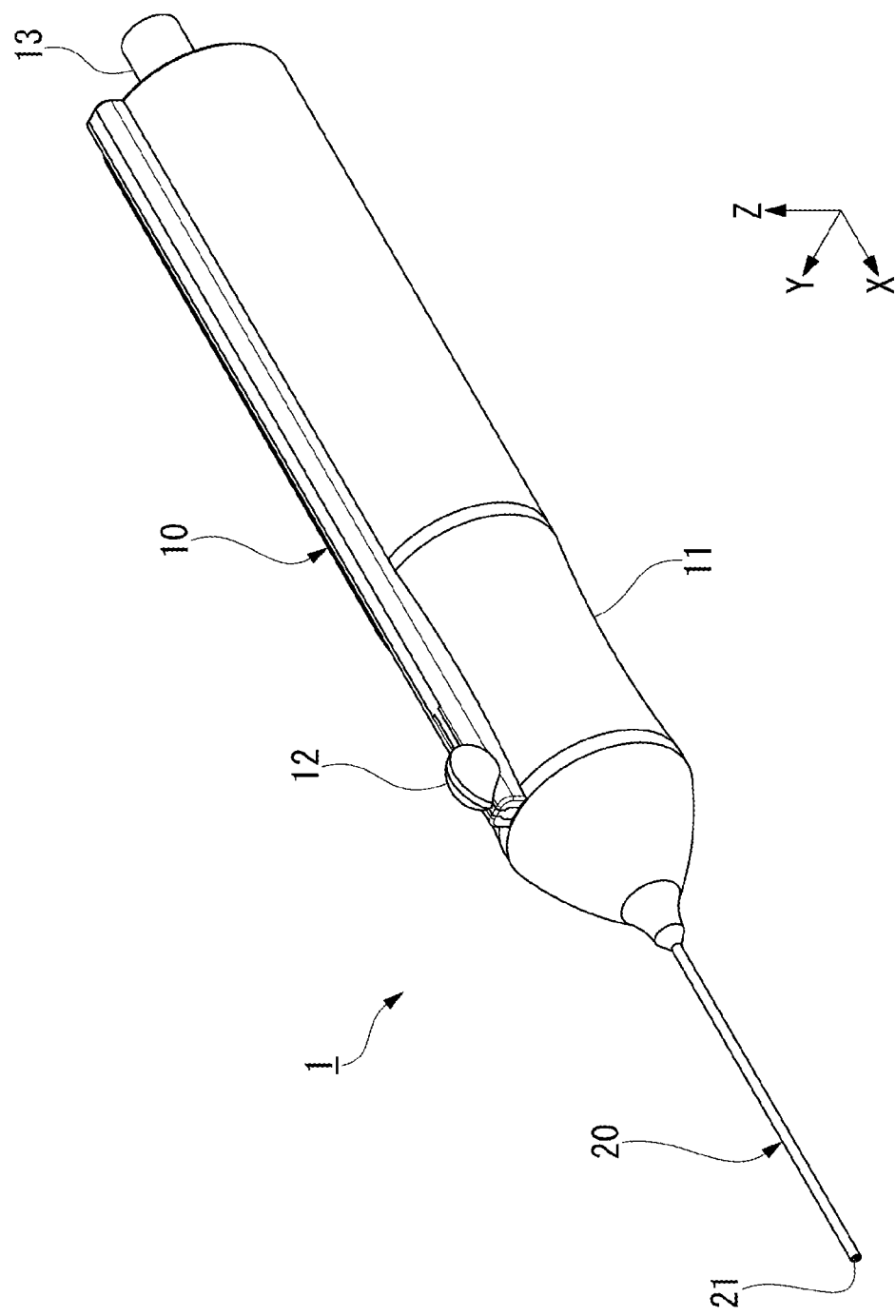
FIG. 2 is a perspective view of an endoscope from which the protective cap according to one or more embodiments of the present invention is removed.
Figure 3:
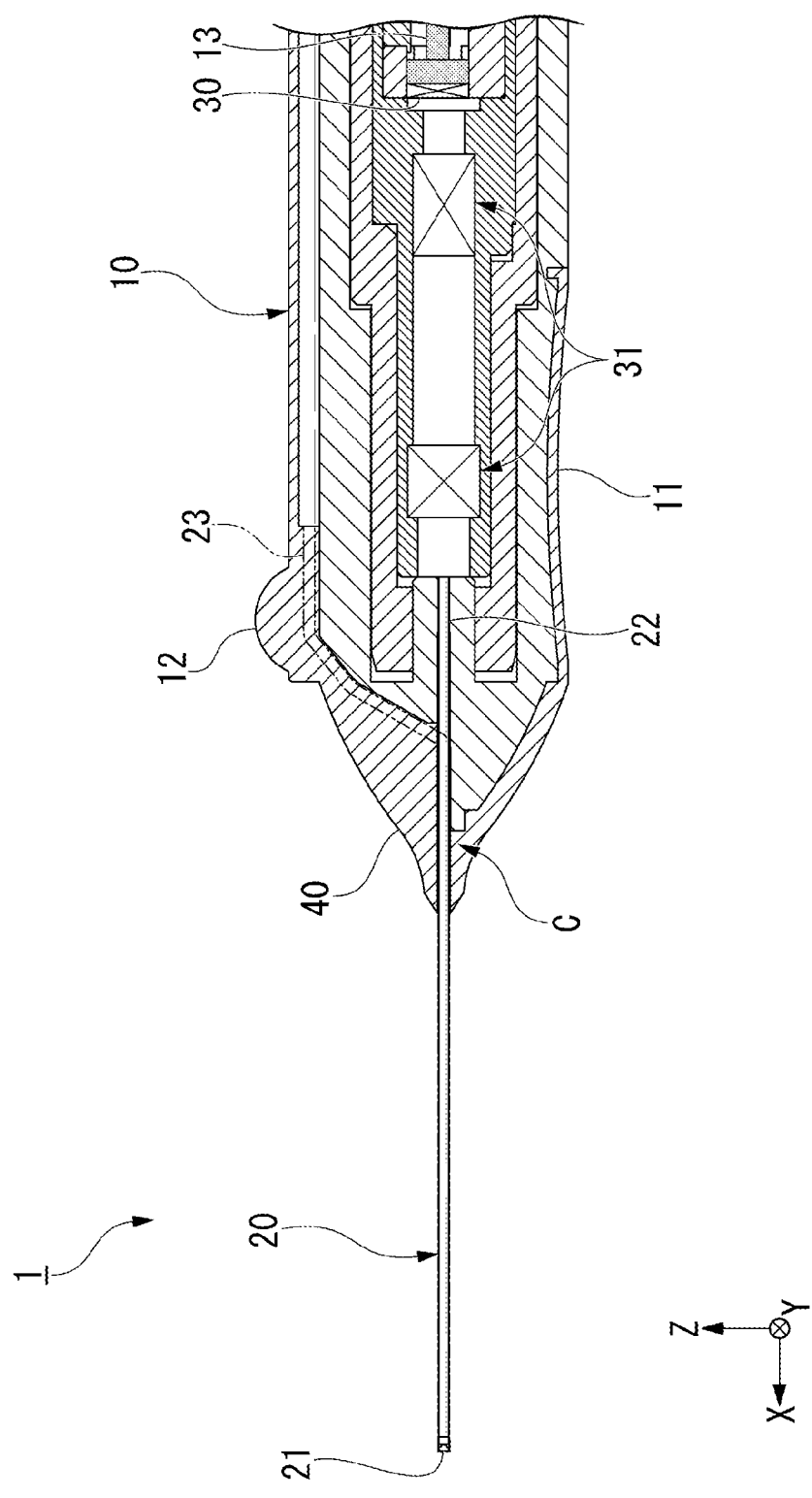
FIG. 3 is a sectional configuration view of the endoscope according to one or more embodiments of the present invention.

FIG. 1 is a perspective view of an endoscope 1 mounted with a protective cap 2 according to one or more embodiments of the present invention. FIG. 2 is a perspective view of the endoscope 1 from which the protective cap 2 according to one or more embodiments of the present invention is removed. FIG. 3 is a sectional configuration view of the endoscope 1 according to one or more embodiments of the present invention.

As shown in these figures, the endoscope 1 includes an endoscope operation unit 10, an insertion observation unit 20 that extends forward from the endoscope operation unit 10, and the protective cap 2 that covers the insertion observation unit 20 and is detachable.

In the following description, the XYZ Cartesian coordinate system may be set, and a positional relationship of respective members may be described with reference to the XYZ Cartesian coordinate system. An X-axis direction is a longitudinal direction in which the insertion observation unit 20 extends, and a Y-axis direction and a Z-axis direction are biaxial orthogonal directions (also referred to as a lateral direction of the insertion observation unit 20) orthogonal to the X-axis direction.

An engagement hole 5 and an engagement protrusion 12 described below are disposed in the Z-axis direction out of the Y-axis direction and the Z-axis direction. Additionally, in the longitudinal direction in which the insertion observation unit 20 extends, the "front" is a tip 21 side (+X side) in the insertion observation unit 20, and the "rear" is a side (−X side, that is, a base end (root) side of the insertion observation unit 20) opposite to the tip 21 in the insertion observation unit 20.

As shown in FIG. 1, the protective cap 2 includes a mounting portion 3 that is mounted on the endoscope operation unit 10, and a tip accommodation portion 4 that extends forward from the mounting portion 3 and covers the insertion observation unit 20. The mounting portion 3 is formed in a substantially cylindrical shape that surrounds an outer periphery of the endoscope operation unit 10. The tip accommodation portion 4 is formed in a substantially bottomed tubular shape that surrounds an outer periphery of the insertion observation unit 20 and the tip 21.

An engagement hole 5 and a plurality of communication holes 6 are formed on the outer periphery of the mounting portion 3. The protective cap 2 is capable of being attached to the endoscope operation unit 10 and detached from the endoscope operation unit 10. The protective cap 2 is mounted on the endoscope operation unit 10 by engaging the engagement protrusion 12 formed on the front side of the endoscope operation unit 10 shown in FIG. 3 with the engagement hole 5. The communication hole 6 allows sterilization of the endoscope operation unit 10 and the insertion observation unit 20 with the protective cap 2 mounted. That is, a sterilizing gas can flow into the protective cap 2 from the communication hole 6.

As shown in FIGS. 2 and 3, the insertion observation unit 20 is formed in the shape of an elongated needle that extends in the X-axis direction. An objective lens is provided at the tip 21 of the insertion observation unit 20. The insertion observation unit 20 includes an image fiber 22 (optical fiber) that transmits a subject image acquired through the objective lens to the endoscope operation unit 10, and an illumination fiber 23 (optical fiber) that emits illumination light forward from the tip 21.

The image fiber 22 is disposed inside a hard outer tube (stainless steel pipe or the like) (not shown). The illumination fiber 23 is also disposed inside a hard outer tube, similar to the image fiber 22. The other end of the illumination fiber 23 passes through a subcutaneous portion of an outer surface of the endoscope operation unit 10 and is connected to an illumination device (light source) (not shown). In addition, instead of the illumination fiber 23, a small illumination device (LED or the like) may be provided at the tip 21 of the insertion observation unit 20.

As shown in FIG. 2, the endoscope operation unit 10 is formed in a substantially pen shape (also referred to as a substantially columnar shape including a conical portion on a front side) having a holding portion 11 on the front side in the X-axis direction. As shown in FIG. 3, an imaging element 30 such as a CCD or CMOS and a re-imaging optical system 31 for re-imaging the subject image transmitted by the image fiber 22 on the imaging element 30 are provided inside the endoscope operation unit 10.

The imaging element 30 converts the re-imaged subject image into electronic image data. As shown in FIG. 2, the electronic image data is transmitted to an image processing device (not shown) via a cable 13 that extends backward from the endoscope operation unit 10. The image processing device displays the electronic image data on a monitor or stores the data in a storage medium.

Next, the configuration of a coupling portion between the endoscope operation unit 10 and the insertion observation unit 20 in the endoscope 1 having the above configuration will be described.

Figure 4:
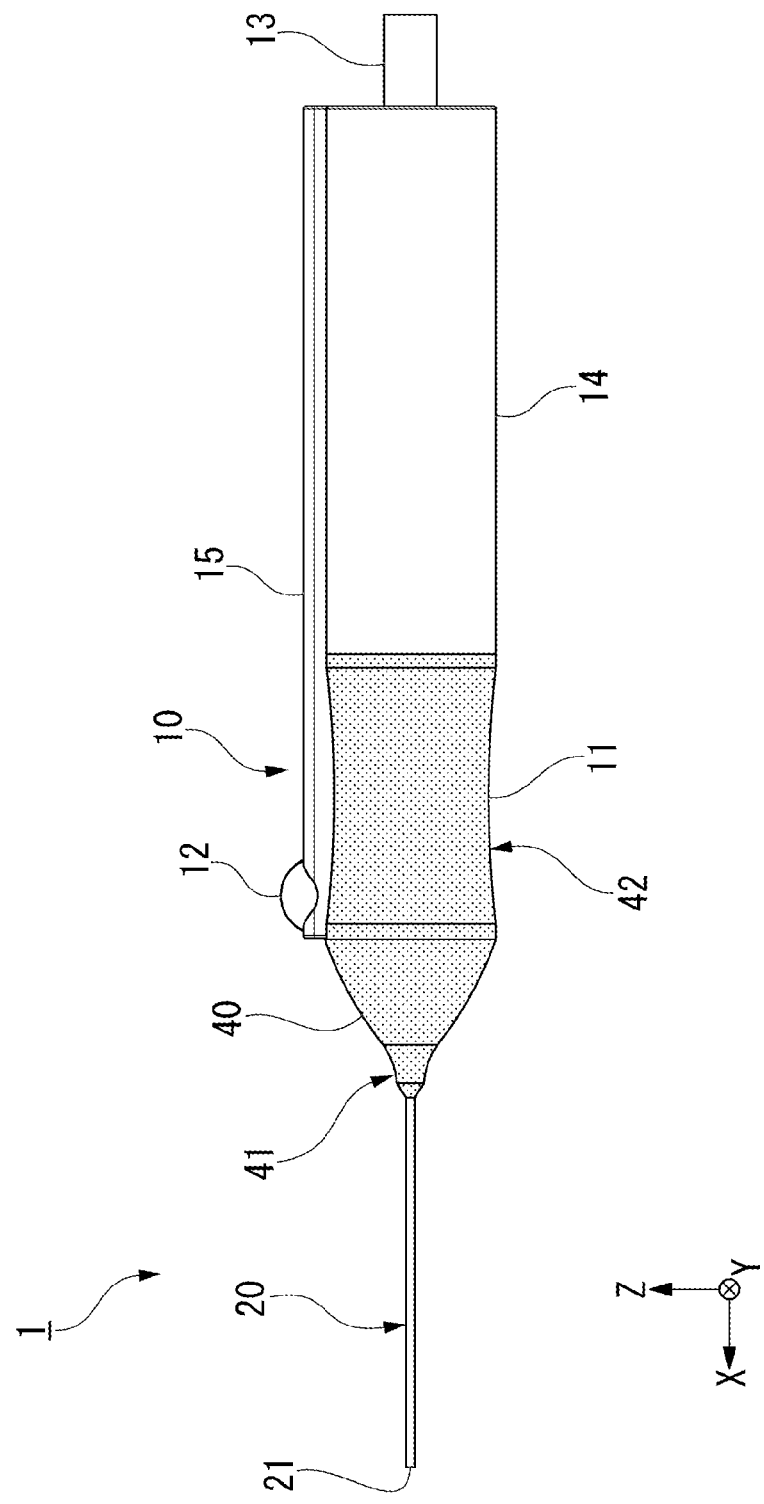
FIG. 4 is a right side view of the endoscope according to one or more embodiments of the present invention.
Figure 5:
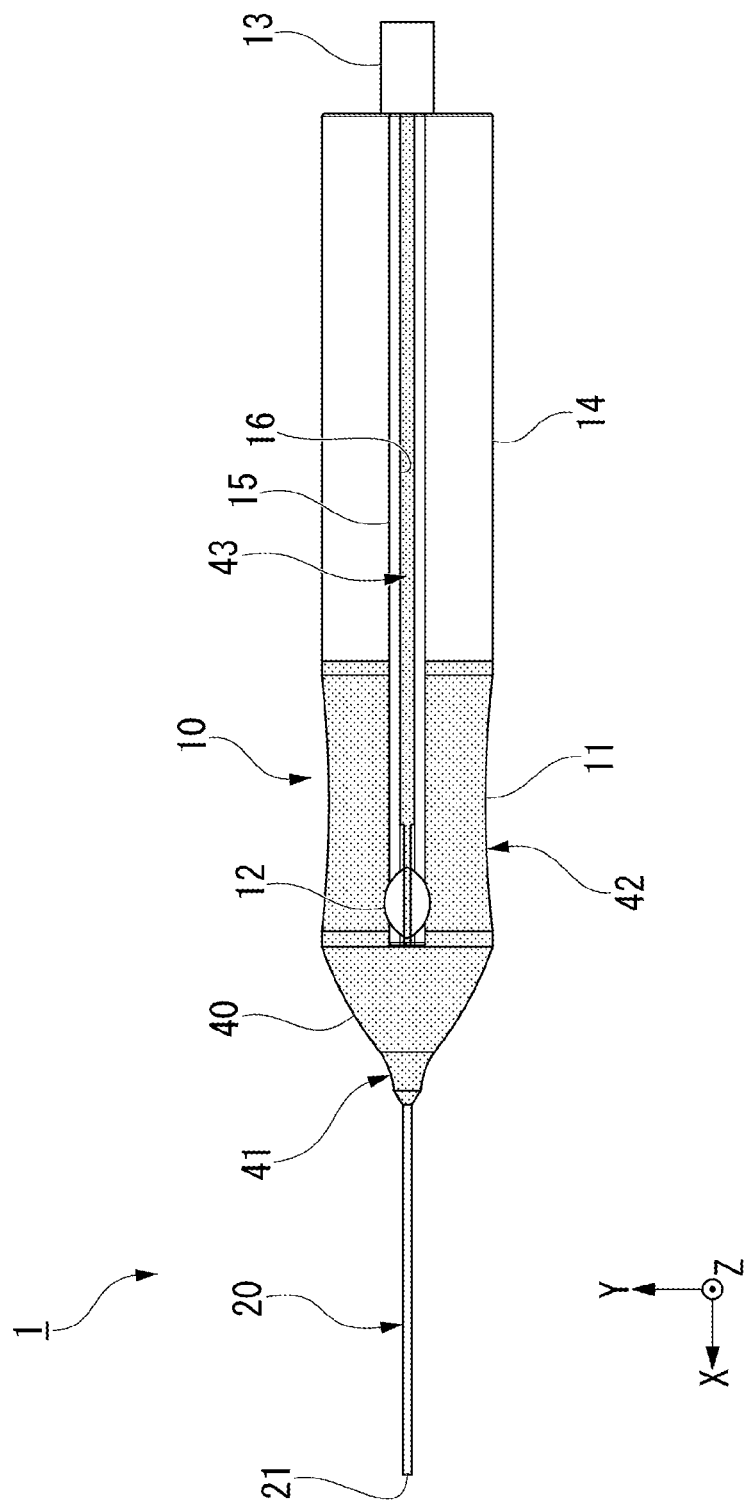
FIG. 5 is a plan view of the endoscope according to one or more embodiments of the present invention.
Figure 6:
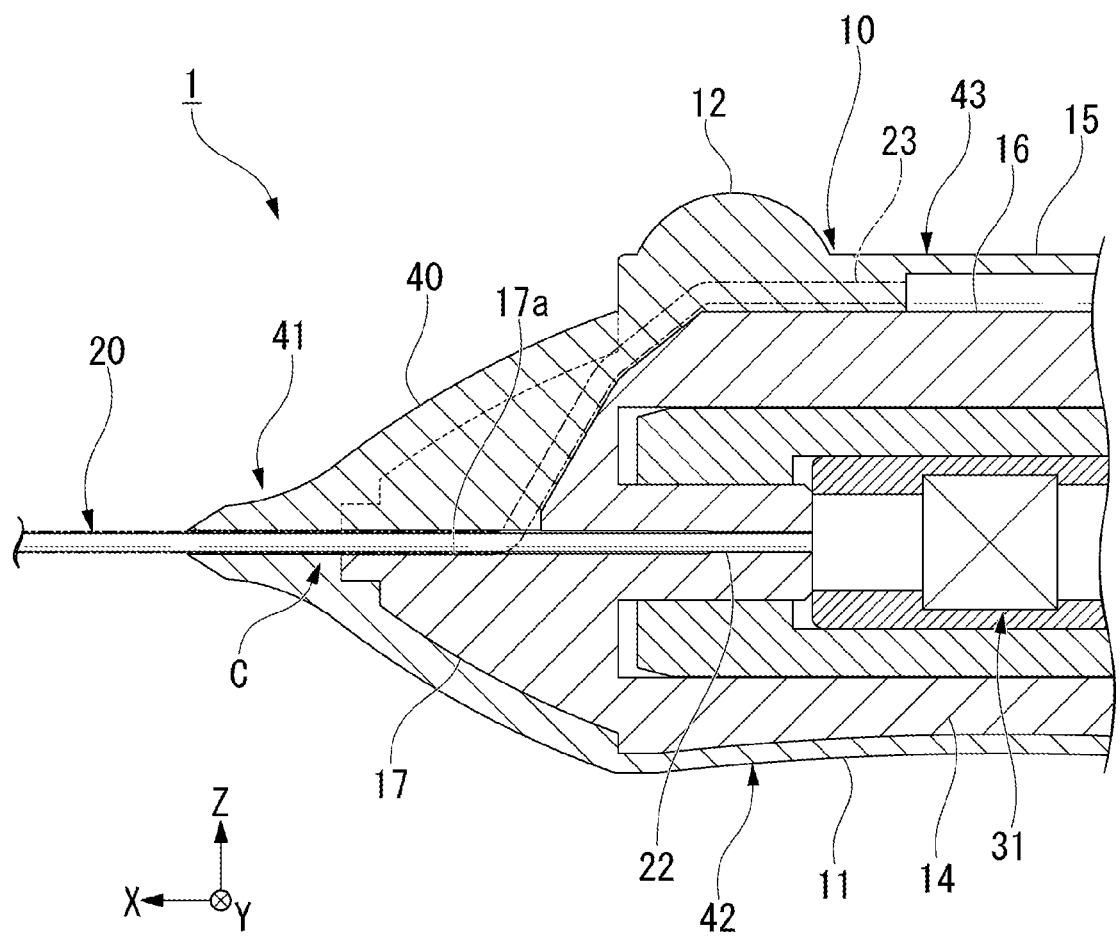
FIG. 6 is a sectional configuration view of a coupling portion between an endoscope operation unit and an insertion observation unit according to one or more embodiments of the present invention.

FIG. 4 is a right side view of the endoscope 1 according to one or more embodiments of the present invention. FIG. 5 is a plan view of the endoscope 1 according to one or more embodiments of the present invention. FIG. 6 is a sectional configuration view of the coupling portion between the endoscope operation unit 10 and the insertion observation unit 20 according to one or more embodiments of the present invention.

As shown in FIGS. 4 and 6, the endoscope 1 includes an elastic body 40 that covers at least the coupling portion C between the endoscope operation unit 10 and the insertion observation unit 20. The elastic body 40 is molded on an outer surface of a case 14 (rigid body) of the endoscope operation unit 10. The elastic body 40 is formed of, for example, a thermosetting elastomer such as urethane rubber, silicone rubber, or fluororubber, or a thermoplastic elastomer.

As shown in FIG. 6, the elastic body 40 has a tapered portion 41, a grip portion 42, and a filling portion 43. The tapered portion 41 is tapered toward the front (the tip 21 of the insertion observation unit 20 side) as shown in FIG. 4 and covers a conical portion 17 to the tip of the case 14 as shown in FIG. 6. The above-described insertion observation unit 20 is disposed on a central axis of the conical portion 17.

The tapered portion 41 covers a conical surface of the conical portion 17 with a substantially constant thickness and extends to the front of an apex (tip) of the conical portion 17. The portion of the tapered portion 41 extending forward from the conical portion 17 is in close contact with the periphery of the insertion observation unit 20 (hard outer tube). The conical portion 17 is formed with a slit 17a that guides the illumination fiber 23 to the insertion observation unit 20 disposed on the central axis. The elastic body 40 is also filled in the slit 17a.

As shown in FIGS. 4 and 5, a rib 15 extending in the longitudinal direction (X-axis direction) is formed on an outer surface of the case 14 of the endoscope operation unit 10. The rib 15 is disposed on a +Z side of the outer surface of the case 14 and extends along the longitudinal direction at a certain height from the outer surface. The above-described engagement protrusion 12 is formed on a front side of the rib 15.

As shown in FIG. 5, a wiring groove 16 of the above-described illumination fiber 23 is formed in the rib 15. The wiring groove 16 is also formed in the engagement protrusion 12 and extends in the longitudinal direction so as to communicate with the slit 17a of the conical portion 17 shown in the above-described FIG. 6. The filling portion 43 of the elastic body 40 fills the wiring groove 16. That is, the illumination fiber 23 is buried in the elastic body 40 inside the wiring groove 16.

As shown in FIG. 4, the grip portion 42 of the elastic body 40 covers a front side of the case 14. The front side of the case 14 is loosely constricted such that a user can easily hold the case 14, and this constriction is covered with the grip portion 42 to serve as the holding portion 11. That is, the endoscope operation unit 10 has the holding portion 11 molded integrally with the elastic body 40.

Meanwhile, as shown in FIG. 6, the coupling portion C between the endoscope operation unit 10 and the insertion observation unit 20 is a portion near the apex of the conical portion 17 of the case 14, that is, a portion including a base end of the insertion observation unit 20 in front of a front end surface of the case 14, specifically, a portion covered with the tapered portion 41. In this coupling portion C, the constraint by the case 14 is eliminated, and bending stress is likely to be applied to the insertion observation unit 20. Particularly, stress concentration is likely to occur near the apex of the conical portion 17. That is, it can be said that the elastic body 40 covers the portion of the insertion observation unit 20 where the stress concentration is likely to occur.

According to the endoscope 1 having the above configuration, even in a structure in which the rigid insertion observation unit 20 (hard outer tube) and the endoscope operation unit 10 (case 14) that is a rigid body are coupled to each other at the base end of the insertion observation unit 20, as shown in FIG. 6, the elastic body 40 is disposed so as to cover the coupling portion C between the endoscope operation unit 10 and the insertion observation unit 20. Therefore, when an external force (for example, an external force in the Y-axis direction or the Z-axis direction) is applied to the insertion observation unit 20, it is possible to suppress the concentration of stress on the base end of the insertion observation unit 20. In particular, the stress concentration can be alleviated at a corner portion where the bending stress is likely to be applied to the insertion observation unit 20, such as the vicinity of the apex of the conical portion 17 and the vicinity of a joining position of the illumination fiber 23, in the base end of the insertion observation unit 20.

In this way, according to one or more embodiments, any damage to the insertion observation unit 20 due to the operation of the endoscope 1 can be suppressed by adopting a configuration including the endoscope operation unit 10, the insertion observation unit 20 extending forward from the endoscope operation unit 10, and the elastic body 40 that covers at least the coupling portion C between the endoscope operation unit 10 and the insertion observation unit 20.

Additionally, in one or more embodiments, as shown in FIGS. 4 to 6, the elastic body 40 has the tapered portion 41 that is tapered toward the front (the tip 21 of the insertion observation unit 20 side). According to this configuration, when an external force is applied to the insertion observation unit 20 while firmly supporting the base end side of the insertion observation unit 20, the concentration of stress on the base end of the insertion observation unit 20 can be further suppressed.

Additionally, in one or more embodiments, the endoscope operation unit 10 has the holding portion 11 molded integrally with the elastic body 40, as shown in FIGS. 4 and 5. According to this configuration, when the user holds the endoscope operation unit 10, the holding portion 11 is held. However, since the holding portion 11 is formed by the elastic body 40 together with the tapered portion 41, the gripping becomes easy, and operability can be improved.

Additionally, in one or more embodiments, the insertion observation unit 20 has the illumination fiber 23 that emits with the illumination light forward from a tip, the endoscope operation unit 10 has the case 14 in which the wiring groove 16 of the illumination fiber 23 is formed as shown in FIG. 5, and the elastic body 40 has the filling portion 43 for filling the wiring groove 16 in which the illumination fiber 23 is wired. According to this configuration, when the elastic body 40 is molded on the outer surface of the case 14 of the endoscope operation unit 10, the wiring groove 16 is filled with the elastic body 40 at the same time. As a result, a wiring retainer (lid or the like) of the illumination fiber 23 is no longer required.

While embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope comprising:
an endoscope operation unit;
an insertion observation unit that extends forward from a base end disposed at the endoscope operation unit toward a tip end that extends in a longitudinal direction of the endoscope;
a coupling portion between the endoscope operation unit and the insertion observation unit; and
an elastic body, made of a thermosetting or thermoplastic elastomer, that is molded on an outer periphery of a tip of the endoscope operation unit, such that it covers and conforms to the coupling portion, wherein
a portion of the elastic body:
    extends from the tip of the endoscope operation unit in the longitudinal direction; and
    concentrically conforms to an outer periphery of the base end of the insertion observation unit, such that the portion of the elastic body is configured to support the base end of the insertion observation unit relative to the endoscope operation unit by resisting a bending stress applied in a direction perpendicular to the longitudinal direction,
the insertion observation unit comprises an illumination fiber configured to emit illumination light from the tip of the insertion observation unit,
the endoscope operation unit comprises a case in which a wiring groove of the illumination fiber is formed,
the illumination fiber is buried inside the wiring groove, and
the wiring groove is filled with the thermosetting or thermoplastic elastomer of the elastic body.

2. The endoscope according to claim 1,
wherein the elastic body comprises a tapered portion that is tapered toward a front of the insertion observation unit.

3. The endoscope according to claim 1,
wherein the endoscope operation unit comprises a holding portion molded integrally with the elastic body.

* * * * *